United States Patent
Cuevas et al.

(10) Patent No.: US 11,395,626 B2
(45) Date of Patent: Jul. 26, 2022

(54) SENSOR FOR INTERVERTEBRAL FUSION INDICIA

(71) Applicant: DePuy Synthes Products, Inc., Raynham, MA (US)

(72) Inventors: Walter Cuevas, Irvine, CA (US); Robert Flower, Sun City, CA (US); Christopher Warren, Aliso Viejo, CA (US)

(73) Assignee: DePuy Synthes Products, Inc., Raynham, MA (US)

( * ) Notice: Subject to any disclaimer, the term of this patent is extended or adjusted under 35 U.S.C. 154(b) by 814 days.

(21) Appl. No.: 15/374,102

(22) Filed: Dec. 9, 2016

(65) Prior Publication Data
US 2017/0231559 A1   Aug. 17, 2017

Related U.S. Application Data

(60) Provisional application No. 62/266,255, filed on Dec. 11, 2015.

(51) Int. Cl.
*A61B 5/00* (2006.01)
*A61B 5/145* (2006.01)
(Continued)

(52) U.S. Cl.
CPC .......... *A61B 5/4848* (2013.01); *A61B 5/0022* (2013.01); *A61B 5/0084* (2013.01);
(Continued)

(58) Field of Classification Search
CPC combination set(s) only.
See application file for complete search history.

(56) References Cited

U.S. PATENT DOCUMENTS

| 4,401,112 A | 8/1983 | Rezaian |
| 4,863,476 A | 9/1989 | Shepperd |

(Continued)

FOREIGN PATENT DOCUMENTS

| DE | 3023353 A1 | 4/1981 |
| EP | 0077159 A1 | 4/1983 |

(Continued)

OTHER PUBLICATIONS

Gray's Anatomy, Crown Publishers, Inc., 1977, pp. 33-54.
(Continued)

*Primary Examiner* — Scott Luan
(74) *Attorney, Agent, or Firm* — BakerHostetler

(57) ABSTRACT

A diagnostic system is provided that provides sensing and transmitting of fusion indicia to determine whether fusion has occurred. In some embodiments, a diagnostic system comprises a spinal implant or graft material; an antenna configured for sending signals to a remote location; a sensor configured for measuring at least one fusion indicia; and a receiver for receiving signals at the remote location. In some embodiments, a method of utilizing a diagnostic system comprises the steps of inserting a spinal implant or graft material within a disc space between two vertebrae; measuring at least one fusion indicia; sending signals to a remote location with an antenna; and receiving signals with a receiver at the remote location.

26 Claims, 7 Drawing Sheets

(51) Int. Cl.
  *A61N 1/05* (2006.01)
  *A61B 5/103* (2006.01)
  *A61B 5/03* (2006.01)
  *A61F 2/44* (2006.01)
  *A61F 5/11* (2006.01)
  *A61B 5/07* (2006.01)
  *A61B 7/00* (2006.01)
  *G16H 40/67* (2018.01)
  *A61N 1/32* (2006.01)
  *A61F 2/28* (2006.01)
  *A61F 2/30* (2006.01)

(52) U.S. Cl.
  CPC ............ *A61B 5/076* (2013.01); *A61B 5/1036* (2013.01); *A61B 5/14542* (2013.01); *A61B 5/4528* (2013.01); *A61B 5/4566* (2013.01); *A61B 5/4851* (2013.01); *A61B 5/6878* (2013.01); *A61B 7/006* (2013.01); *A61F 2/447* (2013.01); *A61F 2/4455* (2013.01); *A61N 1/05* (2013.01); *A61N 1/326* (2013.01); *G16H 40/67* (2018.01); *A61F 2002/286* (2013.01); *A61F 2002/3067* (2013.01); *A61F 2002/30556* (2013.01)

(56) References Cited

U.S. PATENT DOCUMENTS

| | | |
|---|---|---|
| 5,171,278 A | 12/1992 | Pisharodi |
| 5,171,280 A | 12/1992 | Baumgartner |
| 5,308,327 A | 5/1994 | Heaven et al. |
| 5,344,252 A | 9/1994 | Kakimoto |
| 5,390,683 A | 2/1995 | Pisharodi |
| 5,424,773 A | 6/1995 | Saito |
| 5,456,724 A | 10/1995 | Yen et al. |
| 5,514,180 A | 5/1996 | Heggeness et al. |
| 5,554,191 A | 9/1996 | Lahille et al. |
| 5,653,763 A | 8/1997 | Errico et al. |
| 5,658,335 A | 8/1997 | Allen |
| 5,665,122 A | 9/1997 | Kambin |
| 5,693,100 A | 12/1997 | Pisharodi |
| 5,702,391 A | 12/1997 | Lin |
| 5,716,416 A | 2/1998 | Lin |
| 5,762,500 A | 6/1998 | Lazarof |
| 5,865,848 A | 2/1999 | Baker |
| 5,893,889 A | 4/1999 | Harrington |
| 5,976,186 A | 11/1999 | Bao et al. |
| 5,980,522 A | 11/1999 | Koros et al. |
| 6,080,193 A | 6/2000 | Hochshuler et al. |
| 6,109,328 A | 8/2000 | Montana et al. |
| 6,129,763 A | 10/2000 | Chauvin et al. |
| 6,168,597 B1 | 1/2001 | Biedermann et al. |
| 6,176,882 B1 | 1/2001 | Biedermann et al. |
| 6,245,107 B1 | 6/2001 | Ferree |
| 6,368,351 B1 | 4/2002 | Glenn et al. |
| 6,375,682 B1 | 4/2002 | Fleischmann et al. |
| 6,387,130 B1 | 5/2002 | Stone et al. |
| 6,419,704 B1 | 7/2002 | Ferree |
| 6,425,919 B1 | 7/2002 | Lambrecht |
| 6,436,143 B1 | 8/2002 | Ross et al. |
| 6,443,989 B1 | 9/2002 | Jackson |
| 6,454,807 B1 | 9/2002 | Jackson |
| 6,468,310 B1 | 10/2002 | Ralph et al. |
| 6,562,074 B2 | 5/2003 | Gerbec et al. |
| 6,576,016 B1 | 6/2003 | Hochshuler et al. |
| 6,595,998 B2 | 7/2003 | Johnson et al. |
| 6,620,196 B1 | 9/2003 | Trieu |
| 6,685,742 B1 | 2/2004 | Jackson |
| 6,716,247 B2 | 4/2004 | Michelson |
| 6,723,126 B1 | 4/2004 | Berry |
| 6,730,126 B2 | 5/2004 | Boehm et al. |
| 6,733,535 B2 | 5/2004 | Michelson |
| 6,733,635 B1 | 5/2004 | Ozawa et al. |
| 6,740,093 B2 | 5/2004 | Hochshuler et al. |
| 6,773,460 B2 | 8/2004 | Jackson |
| 6,805,695 B2 | 10/2004 | Keith et al. |
| 6,808,537 B2 | 10/2004 | Michelson |
| 6,821,298 B1 | 11/2004 | Jackson |
| 6,830,589 B2 | 12/2004 | Erickson |
| 6,835,206 B2 | 12/2004 | Jackson |
| 6,893,466 B2 | 5/2005 | Trieu |
| 6,923,830 B2 | 8/2005 | Michaelson |
| 6,936,072 B2 | 8/2005 | Lambrecht et al. |
| 6,972,035 B2 | 12/2005 | Michelson |
| 6,997,929 B2 | 2/2006 | Manzi et al. |
| 7,004,945 B2 | 2/2006 | Boyd et al. |
| 7,018,415 B1 | 3/2006 | McKay |
| 7,066,961 B2 | 6/2006 | Michelson |
| 7,094,257 B2 | 8/2006 | Mujwid et al. |
| 7,094,258 B2 | 8/2006 | Lambrecht et al. |
| 7,114,501 B2 | 10/2006 | Johnson et al. |
| 7,118,579 B2 | 10/2006 | Michelson |
| 7,118,598 B2 | 10/2006 | Michelson |
| 7,153,305 B2 | 12/2006 | Johnson et al. |
| 7,179,294 B2 | 2/2007 | Eisermann et al. |
| 7,282,063 B2 | 10/2007 | Cohen et al. |
| 7,306,628 B2 | 12/2007 | Zucherman et al. |
| 7,309,357 B2 | 12/2007 | Kim |
| 7,326,248 B2 | 2/2008 | Michelson |
| 7,410,501 B2 | 8/2008 | Michelson |
| 7,531,002 B2 | 5/2009 | Sutton et al. |
| 7,621,878 B2 | 11/2009 | Ericson et al. |
| D626,233 S | 10/2010 | Cipoletti et al. |
| 7,955,360 B2 | 6/2011 | Michelson |
| 7,985,256 B2 | 7/2011 | Grotz et al. |
| 8,083,741 B2 | 12/2011 | Morgan et al. |
| 8,105,382 B2 | 1/2012 | Olmos et al. |
| 8,147,549 B2 | 4/2012 | Metcalf, Jr. et al. |
| 8,377,136 B2 | 2/2013 | Simonton |
| 8,496,664 B2 | 7/2013 | Michelson |
| 8,518,114 B2 | 8/2013 | Marik |
| 8,551,092 B2 | 10/2013 | Morgan et al. |
| 8,685,095 B2 | 4/2014 | Miller et al. |
| 8,709,088 B2 | 4/2014 | Kleiner et al. |
| 8,771,321 B2 | 7/2014 | Michelson |
| 8,888,850 B2 | 11/2014 | Linares |
| 2002/0183848 A1 | 12/2002 | Ray et al. |
| 2004/0024463 A1 | 2/2004 | Thomas et al. |
| 2004/0097924 A1 | 5/2004 | Lambrecht et al. |
| 2004/0127906 A1 | 7/2004 | Culbert et al. |
| 2004/0172134 A1 | 9/2004 | Berry |
| 2004/0186471 A1 | 9/2004 | Trieu |
| 2004/0215343 A1 | 10/2004 | Hochschuler et al. |
| 2004/0215344 A1 | 10/2004 | Hochschuler et al. |
| 2004/0220580 A1 | 11/2004 | Johnson et al. |
| 2004/0225361 A1 | 11/2004 | Glenn et al. |
| 2005/0043796 A1 | 2/2005 | Grant et al. |
| 2005/0065610 A1 | 3/2005 | Pisharodi |
| 2005/0102202 A1 | 5/2005 | Linden et al. |
| 2005/0130929 A1 | 6/2005 | Boyd |
| 2005/0131406 A1 | 6/2005 | Reiley et al. |
| 2005/0171552 A1 | 8/2005 | Johnson et al. |
| 2005/0182414 A1 | 8/2005 | Manzi et al. |
| 2005/0182418 A1 | 8/2005 | Boyd et al. |
| 2005/0187558 A1 | 8/2005 | Johnson et al. |
| 2005/0187559 A1 | 8/2005 | Raymond et al. |
| 2005/0278026 A1 | 12/2005 | Gordon et al. |
| 2006/0004326 A1 | 1/2006 | Collins et al. |
| 2006/0004457 A1 | 1/2006 | Collins et al. |
| 2006/0004458 A1 | 1/2006 | Collins et al. |
| 2006/0009778 A1 | 1/2006 | Collins et al. |
| 2006/0009779 A1 | 1/2006 | Collins et al. |
| 2006/0009851 A1 | 1/2006 | Collins et al. |
| 2006/0041314 A1 | 2/2006 | Millard |
| 2006/0047341 A1 | 3/2006 | Trieu |
| 2006/0058807 A1 | 3/2006 | Landry et al. |
| 2006/0058880 A1 | 3/2006 | Wysocki et al. |
| 2006/0161166 A1 | 7/2006 | Johnson et al. |
| 2006/0178743 A1 | 8/2006 | Carter |
| 2006/0229629 A1 | 10/2006 | Manzi et al. |
| 2006/0271112 A1* | 11/2006 | Martinson ............ A61B 5/076 607/2 |
| 2006/0276899 A1 | 12/2006 | Zipnick et al. |

(56) References Cited

U.S. PATENT DOCUMENTS

| | | |
|---|---|---|
| 2006/0276901 A1 | 12/2006 | Zipnick et al. |
| 2006/0276902 A1 | 12/2006 | Zipnick et al. |
| 2006/0293663 A1 | 12/2006 | Walkenhorst et al. |
| 2007/0010826 A1 | 1/2007 | Rhoda et al. |
| 2007/0032790 A1 | 2/2007 | Aschmann et al. |
| 2007/0067035 A1 | 3/2007 | Falahee |
| 2007/0073399 A1 | 3/2007 | Zipnick et al. |
| 2007/0118223 A1 | 5/2007 | Allard et al. |
| 2007/0129730 A1 | 6/2007 | Woods et al. |
| 2007/0203491 A1 | 8/2007 | Pasquet et al. |
| 2007/0270968 A1 | 11/2007 | Baynham et al. |
| 2009/0222100 A1 | 9/2009 | Cipoletti et al. |
| 2009/0234456 A1 | 9/2009 | Nycz |
| 2012/0078068 A1 | 3/2012 | Ulmer |
| 2012/0191193 A1 | 7/2012 | Trieu et al. |
| 2013/0060338 A1 | 3/2013 | Hedrick et al. |
| 2013/0103154 A1 | 4/2013 | Trieu et al. |
| 2013/0150970 A1 | 6/2013 | Thaiyananthan |
| 2013/0274883 A1 | 10/2013 | McLuen et al. |
| 2014/0058512 A1 | 2/2014 | Petersheim |
| 2014/0058513 A1 | 2/2014 | Gahman et al. |
| 2014/0107787 A1 | 4/2014 | Stinchfield et al. |
| 2014/0114415 A1 | 4/2014 | Tyber |
| 2014/0277505 A1 | 9/2014 | Mitchell |
| 2015/0148907 A1 | 5/2015 | Kleiner et al. |
| 2017/0196508 A1 * | 7/2017 | Hunter .................. A61F 2/4611 |

FOREIGN PATENT DOCUMENTS

| | | |
|---|---|---|
| EP | 0260044 A1 | 3/1988 |
| WO | 00/67652 A2 | 11/2000 |
| WO | 2008/070863 A2 | 6/2008 |

OTHER PUBLICATIONS

International Search Report received in PCT application No. PCT/US2007/086866 dated Jul. 7, 2008, 2 pages.

Preliminary Report on Patentability received in PCT Application No. PCT/US2007/086866, dated Jun. 10, 2009, in 6 pages.

* cited by examiner

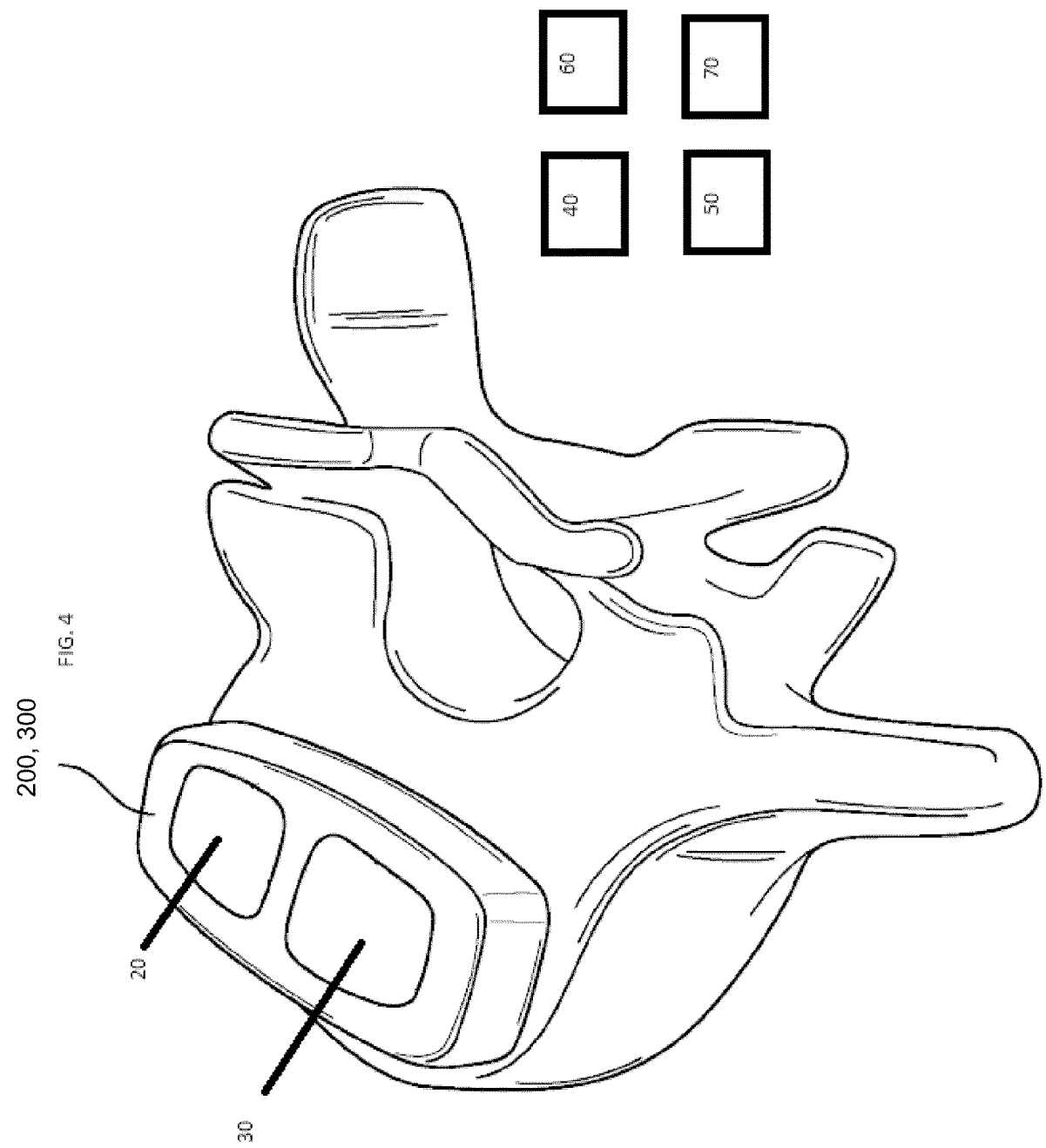

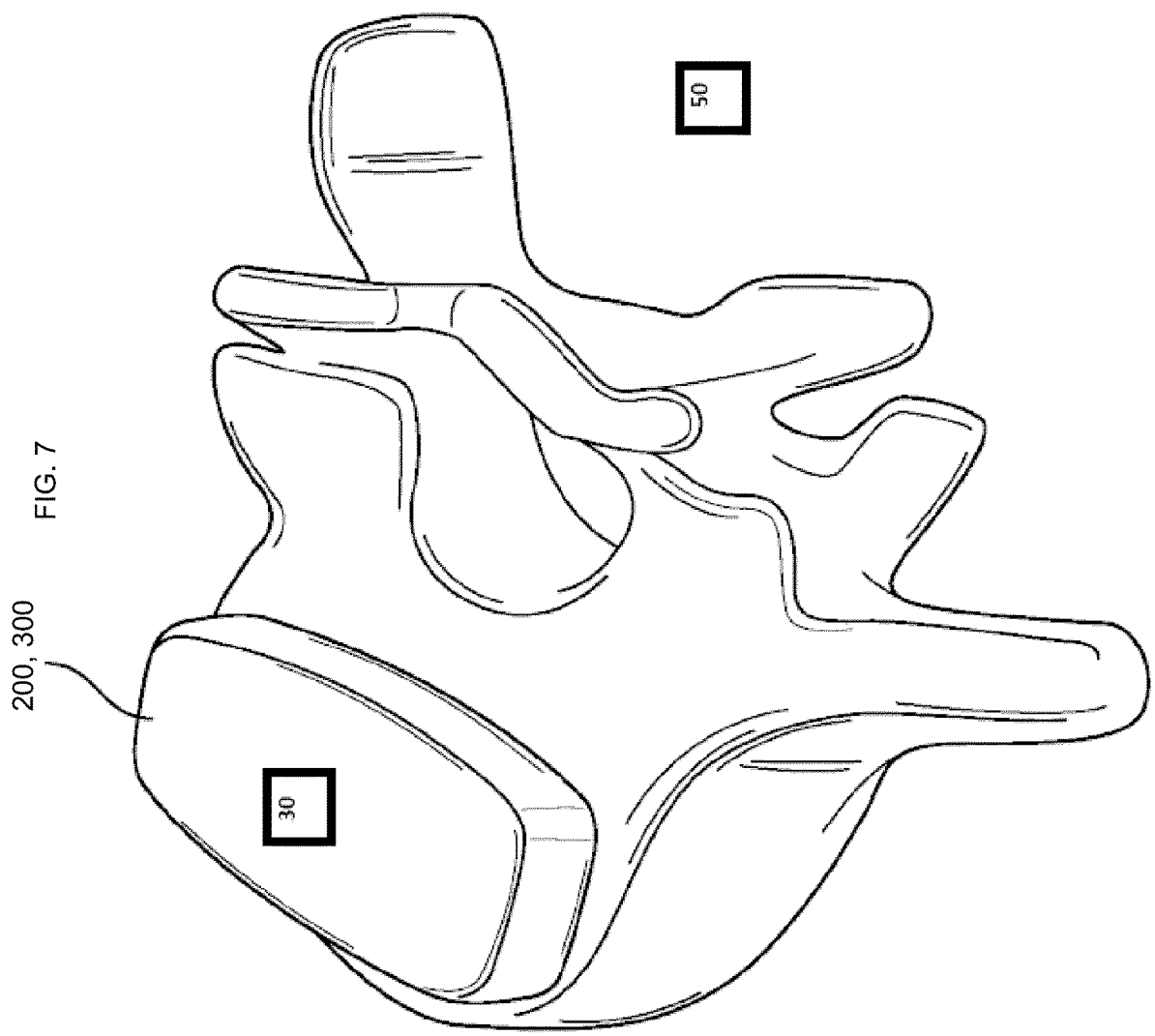

SENSOR FOR INTERVERTEBRAL FUSION INDICIA

CROSS-REFERENCE TO RELATED APPLICATIONS

This present application claims priority under 35 U.S. C. § 119(e) to U.S. Provisional Patent Application No. 62/266,255, filed Dec. 11, 2015, the disclosure of this applications is incorporated by reference herein in its entirety. The present application is related to U.S. application Ser. No. 11/952,900, filed Dec. 7, 2007, which claims the priority benefit of U.S. Provisional Application Ser. No. 60/869,088, filed Dec. 7, 2006. The entire contents of these applications are hereby incorporated by reference herein.

BACKGROUND

Field of the Invention

The present invention relates to medical devices and, more particularly, to a diagnostic systems and methods to indicate successful fusion.

Description of the Related Art

The human spine is a flexible weight bearing column formed from a plurality of bones called vertebrae. There are thirty three vertebrae, which can be grouped into one of five regions (cervical, thoracic, lumbar, sacral, and coccygeal). Moving down the spine, there are generally seven cervical vertebrae, twelve thoracic vertebrae, five lumbar vertebrae, five sacral vertebrae, and four coccygeal vertebrae. The vertebrae of the cervical, thoracic, and lumbar regions of the spine are typically separate throughout the life of an individual. In contrast, the vertebrae of the sacral and coccygeal regions in an adult are fused to form two bones, the five sacral vertebrae which form the sacrum and the four coccygeal vertebrae which form the coccyx.

In general, each vertebra contains an anterior, solid segment or body and a posterior segment or arch. The arch is generally formed of two pedicles and two laminae, supporting seven processes—four articular, two transverse, and one spinous. There are exceptions to these general characteristics of a vertebra. For example, the first cervical vertebra (atlas vertebra) has neither a body nor spinous process. In addition, the second cervical vertebra (axis vertebra) has an odontoid process, which is a strong, prominent process, shaped like a tooth, rising perpendicularly from the upper surface of the body of the axis vertebra. Further details regarding the construction of the spine may be found in such common references as Gray's Anatomy, Crown Publishers, Inc., 1977, pp. 33-54, which is herein incorporated by reference.

The human vertebrae and associated connective elements are subjected to a variety of diseases and conditions which cause pain and disability. Among these diseases and conditions are spondylosis, spondylolisthesis, vertebral instability, spinal stenosis and degenerated, herniated, or degenerated and herniated intervertebral discs. Additionally, the vertebrae and associated connective elements are subject to injuries, including fractures and torn ligaments and surgical manipulations, including laminectomies.

The pain and disability related to the diseases and conditions often result from the displacement of all or part of a vertebra from the remainder of the vertebral column. Over the past two decades, a variety of methods have been developed to restore the displaced vertebra to their normal position and to fix them within the vertebral column. Spinal fusion is one such method. In spinal fusion, one or more of the vertebrae of the spine are united together ("fused") so that motion no longer occurs between them. Thus, spinal fusion is the process by which the damaged disc is replaced and the spacing between the vertebrae is restored, thereby eliminating the instability and removing the pressure on neurological elements that cause pain.

In some methods, spinal fusion can be accomplished by providing an intervertebral implant or bone graft material between adjacent vertebrae to recreate the natural intervertebral spacing between adjacent vertebrae. The bone ingrowth promotes long-term fixation of the adjacent vertebrae. Various posterior fixation devices (e.g., fixation rods, screws etc.) can also be utilize to provide additional stabilization during the fusion process.

SUMMARY

In some embodiments, a diagnostic system is provided. The diagnostic system can include a spinal implant or graft material configured to be inserted within a disc space between two vertebrae. The diagnostic system can include an antenna located in, on or adjacent to the spinal implant, located in, on or adjacent to the graft material, or within the disc space, the antenna configured for sending signals to a remote location. The diagnostic system can include a sensor located in, on or adjacent to the spinal implant, located in, on or adjacent to the graft material, or within the disc space, the sensor configured for measuring at least one fusion indicia. The diagnostic system can include a receiver for receiving signals at the remote location.

In some embodiments, the diagnostic system can include a network that electrically connects the antenna, sensor, and receiver. In some embodiments, the diagnostic system can include a power source located in, on or adjacent to the spinal implant. In some embodiments, the diagnostic system can include a power source located at the remote location. In some embodiments, the antenna is located on the spinal implant. In some embodiments, the antenna is located on the sensor. In some embodiments, the fusion indicia are selected from the group consisting of load, strain, and oxygen level. In some embodiments, the sensor is an oxygen sensor. In some embodiments, the at least one fusion indicia is oxygen level. In some embodiments, the at least one fusion indicia is strain. In some embodiments, the at least one fusion indicia is load. In some embodiments, the at least one fusion indicia is oxygen saturation. In some embodiments, the at least one fusion indicia is light. In some embodiments, the at least one fusion indicia is vibration. In some embodiments, the at least one fusion indicia is pressure.

In some embodiments, a diagnostic system is provided. In some embodiments, the diagnostic system can include a spinal implant or bone graft material configured to be inserted within a disc space between two vertebrae, the spinal implant or bone graft material comprising a piezoelectric material. In some embodiments, the diagnostic system can include an antenna located in, on or adjacent to the spinal implant or within the disc space, the antenna configured for sending signals to a remote location. In some embodiments, the diagnostic system can include a receiver for receiving signals at the remote location.

In some embodiments, the piezoelectric material emits an electric charge when loaded. In some embodiments, the piezoelectric material emits an electric charge to stimulate bone growth. In some embodiments, the electric charge emitted by the piezoelectric material changes as fusion occurs. In some embodiments, the electric charge emitted by the piezoelectric material changes as the spinal implant experiences less loading. In some embodiments, the diagnostic system can include a network that electrically connects the antenna and receiver. In some embodiments, the diagnostic system can include a power source located in, on or adjacent to the spinal implant. In some embodiments, the diagnostic system can include a power source located at the remote location. In some embodiments, the antenna is located on the spinal implant.

In some embodiments, a method of utilizing a diagnostic system is provided. The method can include the step of inserting a spinal implant or graft material within a disc space between two vertebrae. The method can include the step of measuring at least one fusion indicia in, on or adjacent to the implant, in, on or adjacent to the graft material, or within the disc space. The method can include the step of sending signals to a remote location with an antenna located in, on or adjacent to the spinal implant, located in, on or adjacent to the graft material, or within the disc space. The method can include the step of receiving signals with a receiver at the remote location.

In some embodiments, the at least one fusion indicia is oxygen level. In some embodiments, the at least one fusion indicia is strain. In some embodiments, the at least one fusion indicia is load. In some embodiments, the at least one fusion indicia is oxygen saturation. In some embodiments, the at least one fusion indicia is light. In some embodiments, the at least one fusion indicia is vibration. In some embodiments, the at least one fusion indicia is pressure. In some embodiments, the at least one fusion indicia is measured by the implant. In some embodiments, the at least one fusion indicia is measured by a sensor. In some embodiments, the method can include the step of expanding the spinal implant within the disc space. In some embodiments, the method can include the step of activating one or more conducting portion to stimulate bone growth. In some embodiments, measuring at least one fusion indicia occurs after the surgery. In some embodiments, measuring at least one fusion indicia occurs one month after surgery. In some embodiments, measuring at least one fusion indicia occurs one year after surgery.

In some embodiments, a method of utilizing a diagnostic system is provided. The method can include the step of measuring at least one fusion indicia with a sensor located within a body of a patient, the fusion indicia related to fusion of vertebrae. The method can include the step of sending a signal with an antenna located within the body of a patient. The method can include the step of receiving the signal with a receiver at a remote location.

In some embodiments, the at least one fusion indicia is oxygen level. In some embodiments, the at least one fusion indicia is strain. In some embodiments, the at least one fusion indicia is load. In some embodiments, the at least one fusion indicia is oxygen saturation. In some embodiments, the at least one fusion indicia is light. In some embodiments, the at least one fusion indicia is vibration. In some embodiments, the at least one fusion indicia is pressure. The method can include the step of activating one or more conducting portion to stimulate bone growth. In some embodiments, measuring at least one fusion indicia occurs after the surgery. In some embodiments, measuring at least one fusion indicia occurs one month after surgery. In some embodiments, measuring at least one fusion indicia occurs one year after surgery. The method can include the step of coupling the sensor to a spinal implant. The method can include the step of coupling the sensor to any of a plurality of spinal implants. The method can include the step of coupling the sensor to a bone graft material.

In some embodiments, a diagnostic system is provided. In some embodiments, the diagnostic system can include a sensor configured to measure at least one fusion indicia, the sensor configured to be located within a body of a patient, the fusion indicia related to fusion of vertebrae. In some embodiments, the diagnostic system can include an antenna configured to send a signal, the antenna configured to be located within the body of a patient. In some embodiments, the diagnostic system can include a receiver configured for receiving the signal at a remote location.

In some embodiments, the at least one fusion indicia is oxygen level. In some embodiments, the at least one fusion indicia is strain. In some embodiments, the at least one fusion indicia is load. In some embodiments, the at least one fusion indicia is oxygen saturation. In some embodiments, the at least one fusion indicia is light. In some embodiments, the at least one fusion indicia is vibration. In some embodiments, the at least one fusion indicia is pressure. In some embodiments, the diagnostic system can include one or more conducting portion configured to stimulate bone growth. In some embodiments, measuring at least one fusion indicia occurs after the surgery. In some embodiments, measuring at least one fusion indicia occurs one month after surgery. In some embodiments, measuring at least one fusion indicia occurs one year after surgery. In some embodiments, the sensor is coupled to a spinal implant. In some embodiments, the sensor is coupled to any of a plurality of spinal implants. In some embodiments, the sensor is coupled to a bone graft material.

BRIEF DESCRIPTION OF THE DRAWINGS

FIG. 4 is a diagram of a diagnostic system.
FIG. 7 is a diagram of a diagnostic system.

DETAILED DESCRIPTION

In accordance with certain embodiments disclosed herein, an improved diagnostic system and methods are provided that allows the clinician to receive feedback regarding fusion. For example, in some embodiment, one or more intervertebral implants or one or more bone graft materials can be inserted and allowed time to fuse. One or more components of the diagnostic system can detect whether fusion has occurred. One or more components of the diagnostic system can transmit information regarding fusion. One or more components of the diagnostic system can receive information regarding fusion.

The bone graft material can include one or more osteogenic substances. Examples include xenografts, alloplastic grafts, growth factors, synthetic variants such as artificial bone, autogenous bone graft or bone allograft. The bone graft material described herein can be strategically implanted within the disc space to prompt bone ingrowth in the intervertebral space. In some methods of use, once an intervertebral implant is inserted into the intervertebral space, bone graft material can be strategically implanted in, on, or adjacent to the implant to prompt bone ingrowth in the intervertebral space.

The embodiments disclosed herein are discussed in the context of an spinal fusion because of the applicability and usefulness in such a field. As such, various embodiments can be used to properly space adjacent vertebrae in situations where a disc has ruptured or otherwise been damaged. As also disclosed herein, embodiments can also be used as vertebral body replacements. Thus, "adjacent" vertebrae can include those originally separated only by a disc or those that are separated by intermediate vertebra and discs. Such embodiments can therefore tend to recreate proper disc height and spinal curvature as required in order to restore normal anatomical locations and distances. However, it is contemplated that the teachings and embodiments disclosed herein can be beneficially implemented in a variety of other operational settings, for spinal surgery and otherwise.

For example, the implant or bone graft material disclosed herein can also be used as a vertebral body replacement. In such a use, the implant could be used as a replacement for a lumbar vertebra, such as one of the L1-L5 vertebrae. Thus, the implant or bone graft material could be appropriately sized and configured to be used intermediate adjacent vertebrae, or to entirely replace a damaged vertebra. It is contemplated that the implant can be used as an interbody or intervertebral device or can be used to replace a vertebral body entirely. The implant can also be used in vertebral body compression fractures.

Figures 1, 2:
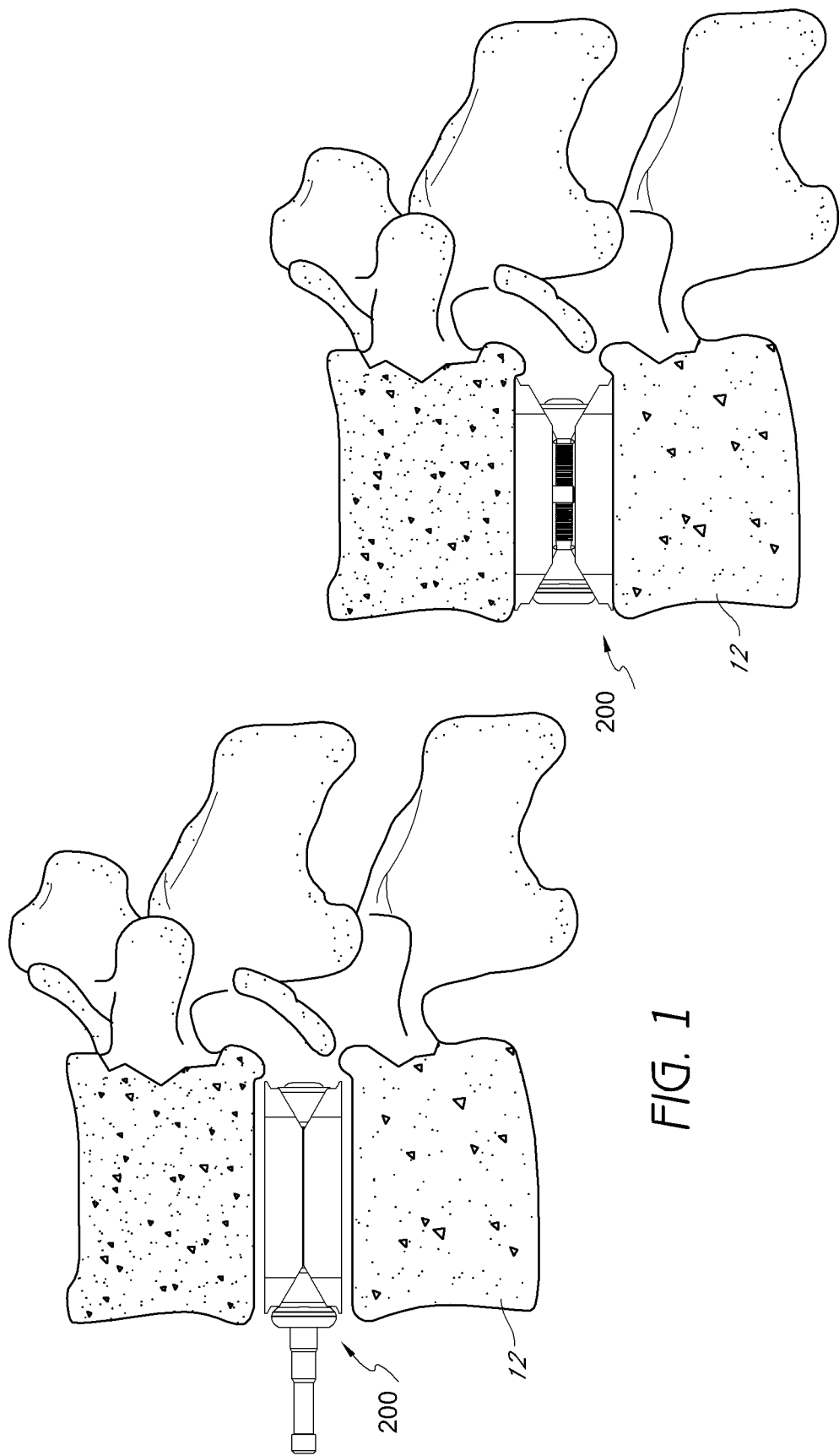
FIG. 1 is a side view of an intervertebral implant in an unexpanded state while positioned intermediate adjacent vertebrae, according to an embodiment.
FIG. 2 is a side view of the intervertebral implant shown in FIG. 1 in an expanded state.

Referring to FIG. 1, there is illustrated a side view of an embodiment of a intervertebral implant 200 in an unexpanded state while positioned generally between adjacent vertebrae of the lumbar portion of the spine 12. FIG. 2 illustrates the intervertebral implant 200 in an expanded state, thereby supporting the vertebrae in a desired orientation and spacing in preparation for spinal fusion. As is known in the art, spinal fusion is the process by which the adjacent vertebrae of the spine are united together ("fused") so that motion no longer occurs between the vertebrae. Thus, the intervertebral implant 200 can be used to provide the proper spacing two vertebrae to each other pending the healing of a fusion. See also U.S. Patent Publication No. 2004/0127906, filed Jul. 18, 2003, application Ser. No. 10/623,193, the entirety of the disclosure of which is hereby incorporated by reference.

According to an embodiment, the implant 200 can be installed in an operation that generally entails one or more of the following method steps. The damaged disc or vertebra can be decompressed, such as by distracting. The subject portion (or entire) disc or vertebra can then be removed. The adjacent vertebrae can be prepared by scraping the exposed adjacent portion or plates thereof (typically to facilitate bleeding and circulation in the area). Typically, most of the nucleus of the disc is removed and the annulus of the disc is thinned out. Although individual circumstances may vary, it may be unusual to remove all of the annulus or to perform a complete discectomy. The implant 200 can then be installed. In some embodiments, distraction of the disc may not be a separate step from placement of the implant; thus, distraction can be accomplished and can occur during placement of the implant. Finally, after implantation of the implant 200, osteogenic substances, such as autogenous bone graft, bone allograft, autograft foam, or bone morphogenic protein (BMP) can be strategically implanted in, on or adjacent to the implant 200 to prompt bone in growth in the intervertebral space. In this regard, as the implant 200 is expanded, the spaces within the implant can be backfilled; otherwise, the implant 200 can be prepacked with biologics.

The intervertebral implant 200 is often used in combination with posterior and/or anterior fixation devices (e.g., rods, plates, screws, etc. that span two or more vertebrae) to limit movement during the fusion process. U.S. Patent Publication No. 2004/0127906 discloses a particularly advantageous posterior fixation device and method which secures two adjacent vertebrae to each other in a trans-laminar, trans-facet or facet-pedicle (e.g., the Boucher technique) application using fixation screws.

It should also be appreciated that in FIGS. 1 and 2 only one intervertebral implant 200 is shown positioned between the vertebrae 12. However, as will be discussed in more detail below, it is anticipated that two, three or more implants 200 can be inserted into the space between the vertebrae. Further, other devices, such as bone screws, can be used on the vertebrae as desired. For example, in a spinal fusion procedure, it is contemplated that one or more implants 200 can be used in conjunction with one or more bone screws and/or dynamic stabilization devices, such as those disclosed in the above-mentioned U.S. Patent Publication No. 2004/0127906, filed Jul. 18, 2003, application Ser. No. 10/623,193. The intervertebral implant 200 is not limited to the shape shown in FIGS. 1 and 2, but may be any shape or size to fit within, or partially within, the disc space.

In some embodiments, the intervertebral implant 200 is static and does not expand, see e.g., FIGS. 4-7. The intervertebral implant 200 can have a fixed dimension in length, width, and/or height. The non-expanding intervertebral implant 200 can have any features of the expandable implant described below. The intervertebral implant 200 can have any shape or size to support vertebrae. The intervertebral implant 200 can have any shape or size to maintain spacing between the endplates. In some embodiments, the intervertebral implant 200 is generally a rectangular block shape. The intervertebral implant 200 can have a pair of side surfaces, a top surface, a bottom surface, a proximal surface and a distal surface. In some embodiments, one or more of the side surfaces, top surface, and bottom surface taper. The taper may facilitate insertion of the intervertebral implant depending on the surgical approach.

Figure 3A:
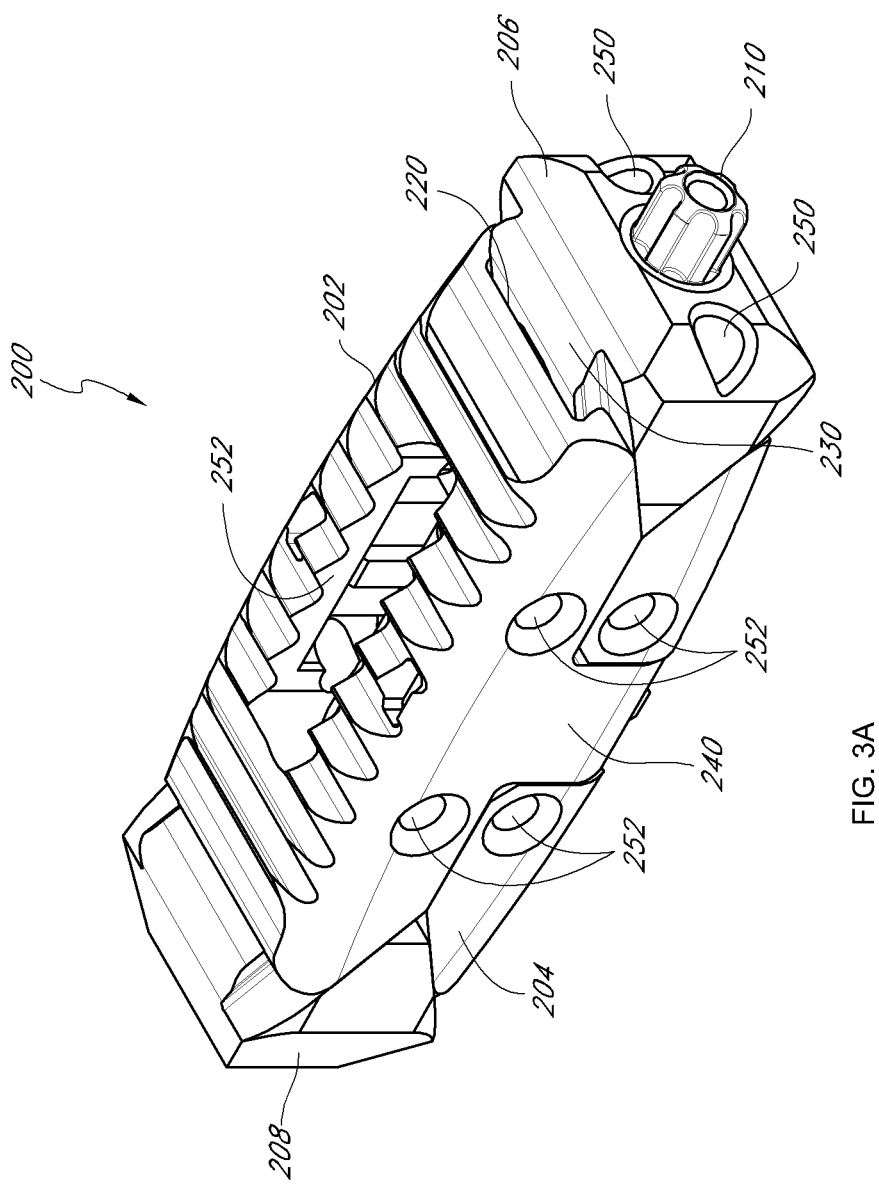
FIG. 3A is a perspective view of an embodiment of an intervertebral implant in an unexpanded state.
Figure 3B:
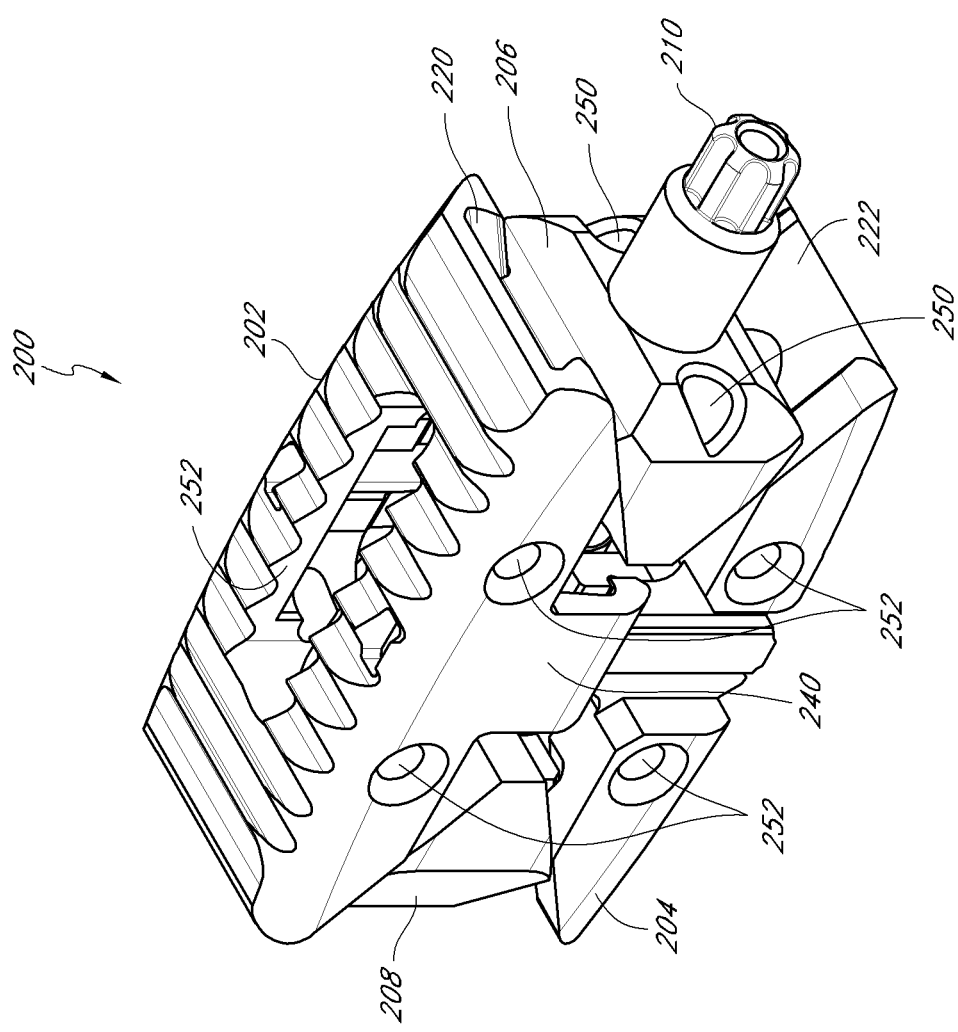
FIG. 3B is a perspective view of the intervertebral implant shown in FIG. 3A wherein the implant is in an expanded state.

In some embodiments, intervertebral implant 200 is expandable. FIGS. 3A and 3B show an embodiment of the intervertebral implant 200 which is expandable. The intervertebral implant 200 can also be introduced into the disc space anteriorly in an anterior lumbar interbody fusion (ALIF) procedure, posterior in an posterior lumbar interbody fusion (PILF) or posterial lateral interbody fusion, from extreme lateral position in an extreme lateral interbody fusion procedure, and transformational lumbar interbody fusion (TLIF), to name a few.

FIG. 3A is a perspective view of an embodiment of an expandable intervertebral implant 200. FIG. 3A shows intervertebral implant 200 in an unexpanded state. The implant 200 can comprise upper and lower body portions 202, 204, proximal and distal wedge members 206, 208, and an actuator shaft 210. In the unexpanded state, the upper and lower body portions 202, 204 can be generally abutting with a height of the implant 200 being minimized. However, the implant 200 can be expanded, as shown in FIG. 3B to increase the height of the implant 200 when implanted into the intervertebral space of the spine. Features of implant 200 are described in U.S. application Ser. No. 11/952,900, filed Dec. 7, 2007 which is incorporated by reference.

It is contemplated that the actuator shaft 210 can be rotated to cause the proximal and distal wedge members to move toward each other, thus causing the upper and lower body portions 202, 204 to be separated. Although the implant is primarily described herein as being used to expand in a vertical direction, it can also be implanted to expand in a horizontal direction in order to increase stability and/or increase surface area between adjacent vertebral bodies. Although the present embodiment is illustrated using this mode of expansion, it is contemplated that other modes of expansion described above (e.g., one way-ratchet type mechanism) can be combined with or interchanged herewith.

The implant 200 can also be made using non-metal materials such as plastics, PEEK™ polymers, and rubbers. Further, the implant components can be made of combinations of PEEK™ polymers and metals. Accordingly, the implant 200 can be at least partially radiolucent, which radiolucency can allow a doctor to perceive the degree of bone growth around and through the implant. The individual components of the implant 200 can be fabricated of such materials based on needed structural, biological and optical properties. The implant 200 may define a gripping structure, such as a plurality of ridges. The gripping structure can promote bony in-growth of the upper and lower endplates of the adjacent vertebrae. Other surface structures can be utilized, including surface structures of varying roughness and texture based on the desired surgical objectives and the anatomy of the joint being fused.

The implant 200 can be configured to include one or more apertures 252 to facilitate osseointegration of the implant 200 within the intervertebral space. As mentioned above, the implant 200 may contain one or more bioactive substances, such as antibiotics, chemotherapeutic substances, angiogenic growth factors, substances for accelerating the healing of the wound, growth hormones, antithrombogenic agents, bone growth accelerators or agents, and the like. Indeed, various biologics can be used with the implant 200 and can be inserted into the disc space or inserted along with the implant 200. The apertures 252 can facilitate circulation and bone growth throughout the intervertebral space and through the implant 200. In such implementations, the apertures 252 can thereby allow bone growth through the implant 200 and integration of the implant 200 with the surrounding materials.

The implant 200 can include plurality of apertures 252 to contain bone graft or growth materials. The apertures 252 can promote bony in-growth for fusion of the adjacent vertebrae. In some embodiments, the implant 200 can include one or more vertical openings extending between the top and bottom surfaces of the implant 200. The vertical openings can have a roughly rectangular shape. In some embodiments, the implant 200 can include one or more horizontal openings extending between the side surfaces of the implant 200. The horizontal openings can have a roughly rectangular shape. The apertures 252 facilitate permanent fusion through and/or around the body of the implant 200.

The intervertebral implant 200 can a component of a diagnostic system 100. The diagnostic system 100 can include one or more additional components. In some embodiments, one or more components of the diagnostic system 100 can be located on or near the intervertebral implant 200. In some embodiments, the diagnostic system 100 includes a sensor 20 or other device to sense one or more fusion indicia. In some embodiments, the diagnostic system 100 includes an antenna 30 or other device to transmit one or more fusion indicia. In some embodiments, the diagnostic system 100 includes a power source 40 or other device to enable sensing or transmission of one or more fusion indicia. In some embodiments, the diagnostic system 100 includes a receiver 50 or other device to receive the transmission of one or more fusion indicia. In some embodiments, the diagnostic system 100 includes additional electronics 60. In some embodiments, the diagnostic system 100 includes an activator 70 to activate a conductive portion of the diagnostic system 100 to promote bone growth. Other components are contemplated, as discussed in more detail herein.

The bone graft material 300 can include one or more osteogenic substances. Examples include autograft or allograft. The bone graft material 300 can be solid or liquid. The bone graft material 300 can have a defined shape. For instance, the bone graft material 300 can have a defined height. The defined height can correspond with the desired separation of adjacent vertebrae. In some methods of use, the bone graft material 300 described herein can be strategically implanted within the disc space to prompt bone ingrowth in the intervertebral space. In some methods of use, once an intervertebral implant 200 is inserted into the intervertebral space, bone graft material 300 can be strategically implanted in, on, or adjacent to the implant to prompt bone ingrowth in the intervertebral space. In some methods of use, the bone graft material 300 is used without an intervertebral implant 200.

FIGS. 4-7 show possible arrangements of the diagnostic system 100, but other configurations are contemplated. The components of the diagnostic system 100 are shown in block form, since they can take a variety of shapes and configurations. Further, as technology advances, the components of the diagnostic system 100 can be replaced with newer devices that sense, transmit, power, and receive fusion indicia. The components of the diagnostic system 100 can be connected via a network. For instance, the network can be a wireless network, a radio network, an electric network or any other network to allow power and/or signals to be transferred between components of the diagnostic system 100.

Figure 5:
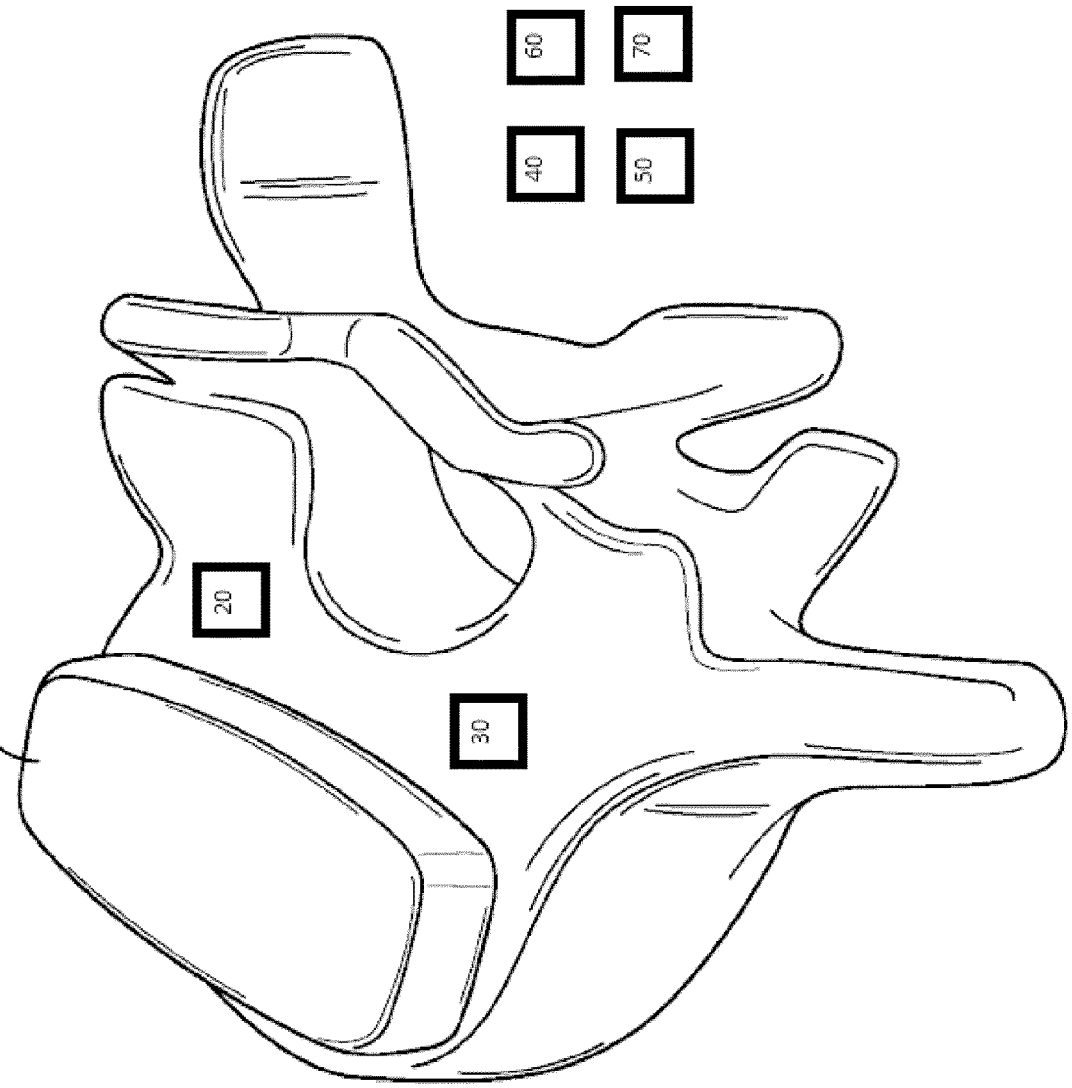
FIG. 5 is a diagram of a diagnostic system.

The components of the diagnostic system 100 are shown in FIGS. 4-7. FIG. 4 shows the sensor 20 and/or the antenna 30 can be located within the disc space. In some embodiments, the sensor 20 and/or the antenna 30 can be integral components with the implant 200, if present. In some embodiments, the sensor 20 and/or the antenna 30 can be integral components with the bone graft material 300, if present. The power source 40, the receiver 50, the other electronics 60, and/or the activator 70 can be located externally to the disc space. In some embodiments, the power source 40, the receiver 50, the other electronics 60, and/or the activator 70 are external to the patient. FIG. 5 shows the sensor 20 and/or the antenna 30 located near the implant 200 and/or bone graft material 300 within the disc space. The power source 40, the receiver 50, the other electronics 60, and/or the activator 70 are located externally to the disc space.

Figure 6:
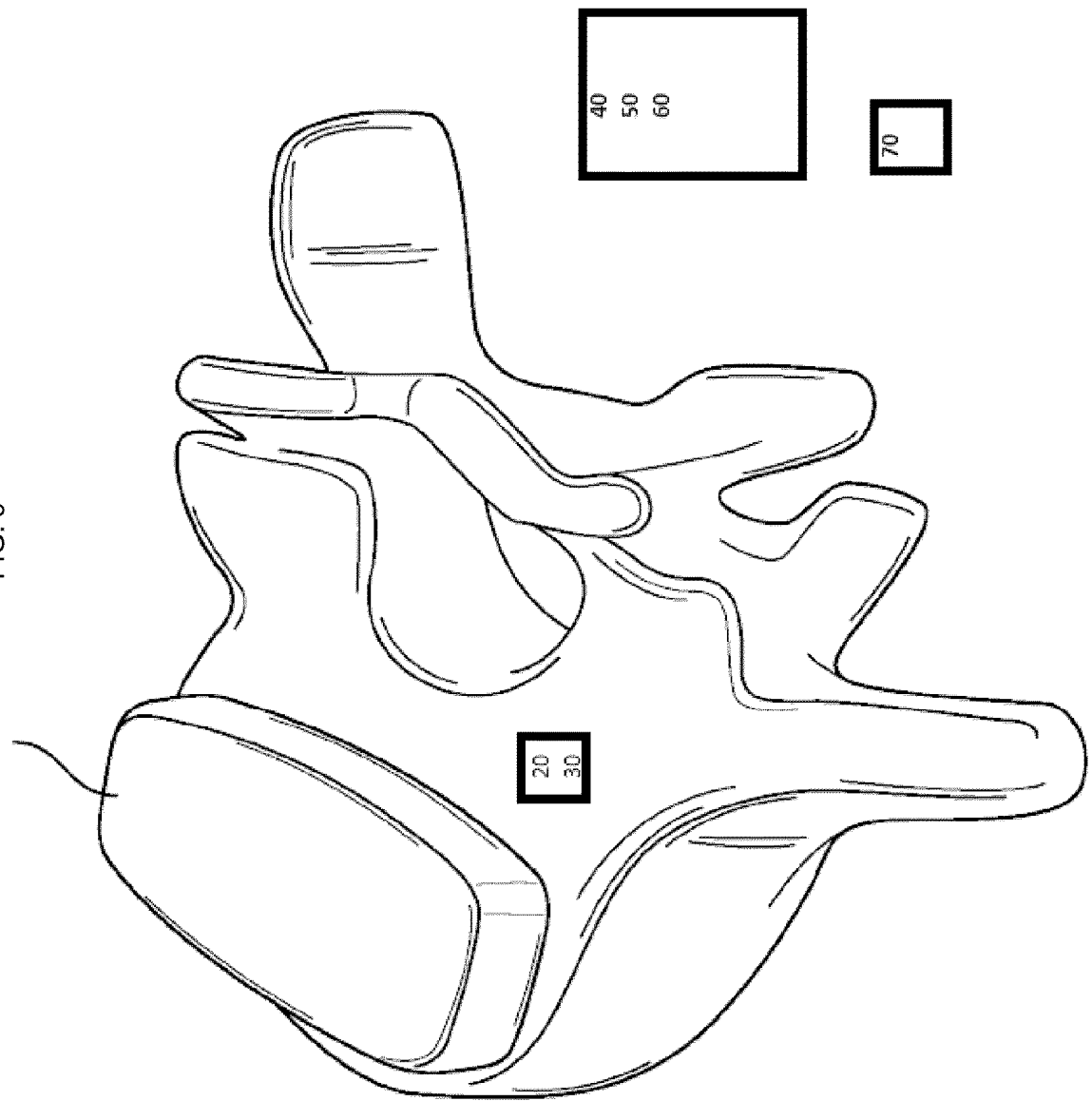
FIG. 6 is a diagram of a diagnostic system.

One or more of the components described herein can be integrated into a single component. FIG. 6 shows the sensor 20 and the antenna 30 located in a combined component within the disc space. The combined component can be located on or near the implant 200, if present, or the bone graft material 300, if present. The power source 40, the receiver 50, the other electronics 60 can be located in a combined component external to the disc space. The activator 70 can be located in a separate component.

The diagnostic system 100 described herein can include fewer components that other systems described herein. FIG. 7 shows the antenna 30 located within the disc space. The receiver 50 can be located externally to the disc space. In some embodiments, the implant 200 or the bone graft material 300 acts as the sensor 20, as described herein. In some embodiments, one or more components generate its own power, as described herein.

In some embodiments, the sensor 20 is integrally formed with the intervertebral implant 200, if present, or the bone graft material 300, if present. In other embodiments, the sensor 20 is placed near the deployment site of the intervertebral implant 200, if present, or the bone graft material 300, if present. The sensor 20 can be placed in any location suitable for sensing the fusion indicia.

In some embodiments, the sensor 20 can be an oxygen sensor. The oxygen sensor 20 can be one of many sensors 20 in the diagnostic system 100. The sensor 20 can be used to sense oxygen levels near the implant 200, if present. For fusion, one desired result is a continuation in bone growth from one vertebra to another vertebra. Such bone growth would encapsulate the intervertebral implant 200. The encapsulation may lead to a decrease in oxygen levels near the intervertebral implant 200. In particular, complete fusion may be detected by a lack of oxygen near the intervertebral implant 200. The sensor 20 can detect the changing oxygen levels near the intervertebral implant 200 as the intervertebral implant 200 resides between the vertebrae. The sensor 20 can be used to sense oxygen levels near the bone graft material 300, if present. The sensor 20 can be placed relative to the bone graft material 300 such that bone growth would encapsulate the sensor 20. The encapsulation may lead to a decrease in oxygen levels sensed by the sensor 20. In particular, complete fusion may be detected by a lack of oxygen. The sensor 20 can detect the changing oxygen levels near the bone graft material 300 as the bone graft material 300 resides between the vertebrae.

In some embodiments, the sensor 20 can sense oxygen saturation. The sensor 20 can measure the percentage of hemoglobin binding sites occupied by oxygen molecules. A low percentage indicates that most hemoglobin binding sites are unoccupied such that most hemoglobin is deoxygenated. The sensor 20 can be a pulse oximeter. The sensor 20 can rely on light absorption characteristics of saturated or oxygenated hemoglobin. The sensor 20 can indicated the level of oxygenated hemoglobin. The sensor 20 can be positioned to monitor oxygenated hemoglobin in a region of the spine. During fusion, the level of oxygenated hemoglobin is expected to decrease.

In some embodiments, the sensor 20 can utilize light to determine whether fusion has occurred. In some embodiments, the sensor 20 can include a plurality of sensors include a light emitter and a light receiver. In some embodiments, the light emitter and a light receiver are placed within the disc space. For instance, the light emitter and a light receiver can be placed on opposite sides of the disc. The path of the light can become obstructed by fusion. The light receiver can detect whether the path of light is obstructed.

The sensor 20 can be any type of sensor configured to detect changes in the environment, such as changes experienced within the body during fusion. Various characteristics are expected to change as the vertebrae fuse. The sensor 20 can sense one or more of these characteristics. The sensors 20 can be placed within the body of a patient in an area to detect the characteristic. The sensor 20 can include one or more sensors configured to measure the same characteristic. The sensor 20 can include one or more sensors configured to measure different characteristics. The sensor 20 can include redundant sensors configured to overlap in detection of a characteristic. The intervertebral implant 200 can include any of the function of the sensor 20 described herein. The bone graft material 300 can include any of the function of the sensor 20 described herein. As described herein, the sensors 20 can be described by name (e.g., geophone, hydrophone, or microphone). The sensor 20 can have any features or additional components essential for the named sensor to function. As described herein, the sensors 20 can be described by function (e.g., measure acoustics, sound and/or vibration). The sensor 20 can be any type of sensor that performs this function. The sensor 20 can be any type of sensor that is configured to perform this function. The sensor 20 can perform a function during a method of use. The sensor 20 can be configured to perform a function in a system.

The sensor 20 can measure acoustics, sound and/or vibration. The sensor 20 can be a geophone, hydrophone, or microphone. For instance, the vibration between adjacent vertebrae is expected to decrease with fusion. The sensor 20 can measure movement, pressure, air flow, blood flow, position, force and/or torque. For instance, the movement between adjacent vertebrae is expected to decrease with fusion. The sensor 20 can measure a chemical reaction, a chemical component, a molecule, and/or a compound. The sensor 20 can be an oxygen sensor as described herein, a plasma sensor, a red blood cell sensor, a white blood cell sensor, or a platelet sensor. For instance, the presence or absence of certain molecules can indicate whether fusion has occurred. For instance, the sensor 20 can be encapsulated during fusion thereby decreasing access to bodily fluids in the disc space. The sensor 20 can measure an infection, nerve damage, muscle disruption, blood clots, nonunion, and/or other complications following surgery. The sensor 20 can measure light, ionizing radiation, ultraviolet light, infrared light, microwaves, and/or radio waves. The sensor 20 can be an optode, infrared point sensor, ion-selective electrode, microwave chemistry sensor, or nondispersive infrared sensor. For instance, the fusion can obstruct the passage of light within the disc space. For instance, the fusion can disrupt the passage of waves or signals within the disc space.

The sensor 20 can sense changes in electric current, electric potential, and/or magnetic field. The sensor 20 can be a current sensor, electroscope, hall effect sensor, MEMS magnetic field sensor, voltage detector, or galvanometer. The sensor 20 can sense changes in flow and/or fluid velocity. For instance, the sensor can detect changes in blood flow following fusion. The sensor 20 can sense changes in position, angle, displacement, distance, speed, motion, and/or acceleration. For instance, the sensor 20 can detect changes in the position of an adjacent vertebra as the adjacent vertebra encroaches during fusion. For instance, the sensor 20 can detect the changes in distance between adjacent vertebrae. For instance, the sensor 20 can detect the rate of fusion including the rate of new bone growth. For instance, the sensor 20 can detect when fused bone makes contact with the sensor 20. For instance, the sensor 20 can detect when the sensor is encapsulated. The sensor 20 can be a capacitive displacement sensor, capacitive sensor, gyroscopic sensor, impact sensor, shock sensor, inclinometer, integrated circuit piezoelectric sensor, laser rangefinder, laser surface velocimeter, LIDAR, linear encoder, linear variable differential transformer, photoelectric sensors, piezocapactive sensors, piezoelectric accelerometers, position sensors, rate sensors, rotary encoder, shock data logger, tilt sensor, stretch sensor, ultrasound thickness gauge, variable reluctance sensor, or velocity sensor. The sensor 20 can measure light, ionizing radiation, ultraviolet light, infrared light, microwaves, and/or radio waves. The sensor 20 can be an optode, infrared point sensor, ion-selective electrode, microwave chemistry sensor, electro-optical sensor, LED as a light sensor, and/or nondispersive infrared sensor. The sensor 20 can measure pressure such as a pressure sensor, pressure gauge, tactile sensor or time pressure gauge. For instance, the sensor 20 can measure a decrease in pressure on the implant 200, if present, or the bone graft 300, if present, when fusion occurs. The sensor 20 can measure force. For instance, the sensor 20 can measure a decrease in force on the implant 200, if present, or the bone graft 300, if present, when fusion occurs. The sensor 20 can be a load cell, level sensor, force gauge, force sensor, piezocapactive pressure sensor, piezoelectric sensor, strain gauge, torque sensor, or viscometer. The sensor 20 can measure heat or temperature such as a thermometer or thermocouple. The sensor 20 can measure proximity or presence, such as the proximity of another bony structure. The sensor 20 can incorporate any sensor technology including digital sensors, image sensors, inductive sensors, intelligent sensors, radar, sonar, ultrasonic, nanotechnology, and/or wireless.

Other sensors 20 are contemplated to sense fusion. In some embodiments, the sensor 20 can sense the load of the vertebrae, such as the changing forces exerted on the intervertebral implant 200, if present, or the bone graft material 300, if present. In particular, the load exerted on the implant 200 or the bone graft material 300 is expected to decrease as the vertebrae fuse. The sensor 20 can sense pressure or tension, such as the changing pressure or tension exerted on the intervertebral implant 200 or the bone graft material 300 by the vertebra. In particular, the pressure or tension exerted on the implant 200 or the bone graft material 300 is expected to decrease as the vertebrae fuse. In some embodiments, the sensor 20 can sense motion. The degree of motion is expected to decrease as the vertebrae fuse.

In some embodiments, the antenna 30 is integrally formed with the intervertebral implant 200, if present, or the bone graft material 300, if present. In other embodiments, the antenna 30 is placed near the deployment site of the intervertebral implant 200, if present, or the bone graft material 300, if present. In some embodiments, the antenna 30 is integrally formed with the sensor 20. In other embodiments, the antenna 30 is placed near the deployment site of the sensor 20. The antenna 30 can be placed in any location suitable for transmitting the fusion indicia.

The antenna 30 can be any device capable of transmitting information. In some embodiments, the antenna 30 can be an electrical device capable of converting power into radio waves. This type of antenna 30 is usually used with a radio receiver. In some embodiments, the antenna 30 can be Radio-frequency identification (RFID) tag. This type of antenna 30 is usually used with a RFID reader. In some embodiments, the antenna 30 transmits an infrared signal.

In some embodiments, the antenna 30 is a relatively thin wire. In other embodiments, the antenna is a radio-conductive material that is wound several times on a woven or non-woven fabric material. The material can be a fabric which can integrate the antenna 30 therein. The antenna 30 can be wound several times so that the antenna 30 can be both long and contained within a small space. A longer antenna 30 is expected to be able to send and receive signals more effectively.

In some embodiments, the power is provided by a power source 40. The power source 40 can be located internally or externally to the patient. In some embodiments, the power source 40 can be a biocompatible battery implanted with the diagnostic system 100. In other embodiments, the power source 40 can be an external battery that sends power to the sensor 20, the antenna 30, the implant 200, and/or the bone graft material 300 through the skin of the patient. The power source 40 can be selected for longevity. For instance, the power source 40 can provide power to the sensor 20, the antenna 30, the implant 200, and/or the bone graft material 300 at selected intervals (e.g., every month, every two months, every three months, every six months, every year, etc.). The power source 40 can provide power at the clinician discretion (e.g., every office visit, every other office visit, at the patient's request, at the clinician's request.)

In some embodiments, the sensor 20, the antenna 30, the implant 200, and/or the bone graft material 300 may be powered using the principle of induction. In this embodiment, one coil of wire is attached within the implanted site. For instance, the wire can be implanted on or near the sensors 20, the antenna 30, the intervertebral implant 200, and/or the bone graft material 300. In this embodiments, one coil of wire is embedded in a receiver 50 or the power source 40 located outside the patient. Excitation in the coil located externally will produce an excitation in the coil located internally.

In some embodiments, the micro-motion inherent in a healing bone may be used as a power source. For instance, a piezoelectric element may be used to receive the micro-motion inherent in healing bone. The piezoelectric element may be coupled to one or more components of the diagnostic system 100. In some embodiments, the piezoelectric element is coupled or integrally formed with the sensor 20. In some embodiments, the piezoelectric element is coupled or integrally formed with the antenna 30. In some embodiments, the piezoelectric element is coupled or integrally formed with the implant 200. In some embodiments, the piezoelectric element is coupled or integrally formed with the bone graft material 300. The piezoelectric element can generate power for the diagnostic system 100.

In some embodiments, components of the diagnostic system 100 can be self-powered and not require a separate power source 40. In some embodiments, the components of the diagnostic system 100 are piezoelectric such that signals detected by these components or other signals provide power to the diagnostic system 100. In other embodiments, the components of the diagnostic system 100 utilize energy harvesting to recharge the power source 40 or store energy for use by the components. For instance, the components of the diagnostic system 100 can utilize energy generated by the patient's motion. Additional and/or alternative sources of power may be utilized.

The receiver 50 can be located internally or externally to the patient. In some embodiments, the receiver 50 can receive radio signals. In some embodiments, the receiver 50 can receive RF signals. The receiver 50 can be configured to receive any type of signal from the corresponding antenna 30. In some embodiments, the receiver 50 can provide the fusion indicia to the clinician. For instance, the receiver 50 can include a display to represent the fusion indicia. For instance, the receiver 50 can generate a report regarding the fusion indicia. The receiver 50 can have a processor that enables the receiver 50 to receive and process the signal from the sensor 20, the antenna 30, the implant 200, and/or the bone graft material 300. In some embodiments, the receiver 50 can transmit data to a computer system for further processing.

In some embodiments, the receiving device 50 is a wireless handheld computer or telephone. In some embodiments, the receiver 50 can request information from the components of the diagnostic system 100, receive information sent by the diagnostic system 100, and/or store information from the diagnostic system 100. For example, the clinician may place the receiving device 50 near or over the intervertebral implant 200, if present, or the bone graft material 300, if present. The receiving device 50 can receive the fusion indicia from the antenna 30 such as strain and oxygen data from one or more sensors 20.

In some embodiments, software associated with the receiving device 50 may analyze the data and provide summary to a clinician. Such a summary may comprise discrete values taken from the individual sensors 20, the antenna 30, the implant 200, and/or the bone graft material 300. The summary may also comprise a graph or other visual display. In some embodiments, the receiver 50 can be connected to a network for transmission of the fusion indicia. In some methods, the clinician utilizes the receiver 50. In other methods, the patient utilizes the receiver 50 to obtain the data from the diagnostic system 100. The patient can send this data to the clinician using the network, such as the internet or telephone network. In some embodiments, any communication between the receiver 50 and network is encrypted or otherwise secured. In some methods, data can be collected on a regular interval (e.g. daily, weekly, monthly, etc.).

In some embodiments, the diagnostic system 100 includes additional electronics 60. In some embodiments, the electronics 60 can control components of the diagnostic system 100. In some embodiments, the electronics 60 can include a processor. In some embodiments, the electronics 60 can include a microchip. In some embodiments, the electronics 60 can include a data log for recording the fusion indicia. Other components of the electronics 60 can include a signal conditioner and multiplexer. In some embodiments, the electronics 60 can include microelectromechanical systems ("MEMS") devices. In some embodiments, one or more subcomponents of the electronics 60 can be disposed within the disc space. In other embodiments, one or more subcomponents of the electronics 60 can be disposed external to the patient. In some embodiments, the electronics 60 can be wireless. In other embodiments, the electronics 60 can be hard-wired to one or more other components of the diagnostic system 100.

In some embodiments, the implant 200 acts as a sensor 20. The intervertebral implant 200 can provide the ability to sense one or more fusion indicia. The diagnostic system 100 can provide the ability to transmit one or more fusion indicia. The diagnostic system 100 can allow a clinician to monitor a patient after spinal surgery, in particular to monitor the degree of fusion of the vertebrae. This embodiment is shown in FIG. 7. In some embodiments, the bone graft material 300 acts as a sensor 20. The bone graft material 300 can provide the ability to sense one or more fusion indicia. The diagnostic system 100 can provide the ability to transmit one or more fusion indicia. The diagnostic system 100 can allow a clinician to monitor a patient after spinal surgery, in particular to monitor the degree of fusion of the vertebrae. This embodiment is shown in FIG. 7.

The intervertebral implant 200, if present, can include a piezoelectric material to generate a voltage and/or current. The bone graft material 300, if present, can include a piezoelectric material to generate a voltage and/or current. Piezoelectric materials accumulate electric charge in response to applied mechanical stress. The piezoelectric effect is reversible, such that piezoelectric materials can both generate electric charge resulting from applied force and generate a mechanical strain resulting from an applied electrical field. Examples of piezoelectric materials include quartz, sucrose, topaz, bone, tendon, collagen, ceramics including Barium titanate, Sodium tungstate, Potassium niobate, Lithium niobate, and zinc oxide, Sodium potassium niobate, Bismuth ferrite, semiconductors, polymers including Polyvinylidene fluoride.

The intervertebral implant 200, if present, can emit voltage and/or current when loaded and unloaded. This voltage and/or current can be used to stimulate bone growth. In some embodiments, the emitted voltage and/or current can allow implant 200 to function as the sensor 20 described herein. For instance, as the bone heals, the load experienced by the implant 200 is expected to decrease. This change in loading will alter the emitted voltage and/or current. In some embodiments, the antenna 30 described herein can transmit information related to the change in emitted voltage and/or current. In some embodiments, the receiver 50 described herein can received information related to the change in emitted voltage and/or current. In other embodiments, the receiver 50 can directly measure the change in emitted voltage and/or current without the antenna 30. In some embodiments, no additional sensors 20 are provided in the diagnostic system 100. In some embodiments, the implant 200 itself is a sensor 20.

The bone graft material 300, if present, can emit voltage and/or current when loaded and unloaded. This voltage and/or current can be used to stimulate bone growth. In some embodiments, the emitted voltage and/or current can allow bone graft material 300 to function as the sensor 20 described herein. For instance, as the bone heals, the load experienced by the bone graft material 300 is expected to decrease. This change in loading will alter the emitted voltage and/or current. In some embodiments, the antenna 30 described herein can transmit information related to the change in emitted voltage and/or current. In some embodiments, the receiver 50 described herein can received information related to the change in emitted voltage and/or current. In other embodiments, the receiver 50 can directly measure the change in emitted voltage and/or current without the antenna 30. In some embodiments, no additional sensors 20 are provided in the diagnostic system 100. In some embodiments, the bone graft material 300 itself is a sensor 20.

In some embodiments, a material can be added to the bone graft material 300 to emit a signal. The additive material can emit a signal such as when it experiences a load. The additive material can emit a signal under certain environmental conditions such as the lack of oxygen. The additive material can sense a fusion indicia to determine whether fusion has occurred.

In some embodiments, the implant 200, if present, can be a conductor or includes conductive portions. The implant 200 can be in communication with an activator 70. The activator 70 can be internal or external to the patient. The activator 70 can supply electric charge to the conductor or conductive surfaces. The activator 70 can send a stimulation signal to the implant 200 to selectively activate the conductor or conductive portions. In some embodiments, the intervertebral implant 200 or a portion thereof is configured to emit energy received from the activator 70. The conductor or conductive surfaces can act as electrodes for the stimulation of bone growth. Sustained application of electricity has been found to stimulate both bone resorption and bone growth in-vivo. The activator 70 can alter the polarity to stimulate either resorption or growth.

The activator 70 can stimulate the implant 200 with an electrical current. The conductors or conductive portions can be placed near bone or other regions to stimulate bone regrowth. Software within the activator 70 can be used to determine the appropriate voltage or current to stimulate bone growth. The software can also set a threshold level of voltage or current. The activator 70 can display a signal to the clinician when voltage or current is being applied. The diagnostic system 100 can acquire additional information from sensors 20, if present. For instance sensors 20 can determine the level of current or voltage experienced by different regions of the intervertebral space.

The implant 200 may have different configurations of conductors or conductive surfaces depending upon the surgical approach, the joint being fused, and the surrounding tissue configuration. During placement of the implant 200, the conductor can be activated to establish communication between the implant 200 and the activator 70. The implant 200 itself can stimulate bone growth by being activated by the activator 70. The input to the implant 200 can be determined in real-time. The feedback from associated sensors 20 can be determined in real-time.

In some embodiments, the bone graft material 300, if present, can be a conductor or includes conductive portions. The bone graft material 300 can be in communication with an activator 70. The activator 70 can be internal or external to the patient. The activator 70 can supply electric charge to the conductor or conductive surfaces. The activator 70 can send a stimulation signal to the bone graft material 300 to selectively activate the conductor or conductive portions. In some embodiments, the bone graft material 300 or a portion thereof is configured to emit energy received from the activator 70. The conductor or conductive surfaces can act as electrodes for the stimulation of bone growth. Sustained application of electricity has been found to stimulate both bone resorption and bone growth in-vivo. The activator 70 can alter the polarity to stimulate either resorption or growth.

The activator 70 can stimulate the bone graft material 300 with an electrical current. The conductors or conductive portions can be placed near bone or other regions to stimulate bone regrowth. Software within the activator 70 can be used to determine the appropriate voltage or current to stimulate bone growth. The software can also set a threshold level of voltage or current. The activator 70 can display a signal to the clinician when voltage or current is being applied. The diagnostic system 100 can acquire additional information from sensors 20, if present. For instance sensors 20 can determine the level of current or voltage experienced by different regions of the intervertebral space.

The bone graft material 300 may have different configurations of conductors or conductive surfaces depending upon the surgical approach, the joint being fused, and the surrounding tissue configuration. During placement of the bone graft material 300, the conductor can be activated to establish communication between the bone graft material 300 and the activator 70. The bone graft material 300 itself can stimulate bone growth by being activated by the activator 70. The input to the bone graft material 300 can be determined in real-time. The feedback from associated sensors 20 can be determined in real-time.

The diagnostic system 100 is capable of enabling a clinician to monitor a patient after spinal surgery. In some methods of use, the intervertebral implant 200 can be implanted into the body of the patient. In some methods of use, the bone graft material 300 can be implanted into the body of the patient. In some methods of use, the intervertebral implant 200 and the bone graft material 300 can be implanted into the body of the patient. For instance, the bone graft material 300 can be located on, in or adjacent to the intervertebral implant. One or more substances can be added to the disc space to promote fusion.

In some methods, the sensor 20 is separately implanted into the body of the patient. In other methods, the sensor 20 is implanted in conjunction with the intervertebral implant 200. In other methods, the sensor 20 is implanted in conjunction with the bone graft material 300. For instance, the sensor 20 can be located on, in, or adjacent to the intervertebral implant 200. The sensor 20 can be located on, in, or adjacent to the bone graft material 300. The sensor 20 can be located within the disc space.

In some methods, the antenna 30 is separately implanted into the body of the patient. In other methods, the antenna 30 is implanted in conjunction with the intervertebral implant 200. In other methods, the antenna 30 is implanted in conjunction with the bone graft material 300. For instance, the antenna 30 can be located on, in, or adjacent to the intervertebral implant 200. The antenna 30 can be located on, in, or adjacent to the bone graft material 300. The antenna 30 can be located within the disc space.

In some methods, the power source 40 is separately implanted into the body of the patient. In other methods, the power source 40 is implanted in conjunction with the intervertebral implant 200. In other methods, the power source 40 is implanted in conjunction with the bone graft material 300. For instance, the power source 40 can be located on, in, or adjacent to the intervertebral implant 200. The power source 40 can be located on, in, or adjacent to the bone graft material 300. The power source 40 can be located within the disc space.

The sensor 20, the antenna 30, the implant 200, the bone graft material 300, and/or the power source 40 can be tested to ensure proper connectivity. The spinal surgery is completed. Any entry points into the surgical space are closed. The patient recovers from spinal surgery. At any point after implantation, the diagnostic system 100 can be activated to transmit data. The sensor 20, if present, the implant 200, if present, and/or the bone graft material 300, if present, can be configured to sense the fusion indicia. The antenna 30, if present, can transmit the fusion indicia to the receiver 50. The power source 40, if present, can supply power to the sensor 20, the antenna, the implant 200, and/or the bone graft material 300. The clinician can receive the fusion indicia with the receiver 50 to determine whether fusion has occurred.

In some methods, the sensor 20, the implant 200, and/or the bone graft material 300 functions as an oxygen sensor. The sensor 20, implant 200, and/or bone graft material can sense the oxygen levels near or around the sensor 20, if present, near or around the intervertebral implant 200, if present, near or around the bone graft material 300, if present, or within the disc space. The fusion indicia can be routed to the antenna 30. The antenna 30 can transmit the fusion indicia to the receiver 50. The receiver 50 can receive the fusion indicia from the antenna 30. Based on the oxygen levels, the clinician can determine whether fusion has occurred In some embodiments, the sensor 20, the implant 200, and/or the bone graft material 300 functions as a load sensor. The sensor 20, implant 200, and/or bone graft material can be inserted between two vertebrae in sense the load carried by the sensor 20, if present, the intervertebral implant 200 if present, or the bone graft material 300. During fusion, the load exerted on the sensor 20, if present, the implant 200, if present, and/or the bone graft material 300, if present, is expected to decrease. Such a sensor 20, implant 200, and/or bone graft material can detect the interaction between the sensor 20 and the spine, if present, the interaction between the spine and the intervertebral implant 200, if present, or the interaction between the spine and the bone graft material 300, if present. The fusion indicia can be routed to the antenna 30. The antenna 30 can transmit the fusion indicia to the receiver 50. The receiver 50 can receive the fusion indicia from the antenna 30. Based on the load, the clinician can determine whether fusion has occurred.

The load sensor 20, the implant 200, and/or the bone graft material 300 can be implanted in any location. In some methods, the sensor 20, the implant 200, and/or the bone graft material 300 is implanted in an excised part of a spine. The stress or load experienced by the sensor 20, the implant 200, and/or the bone graft material 300 can indicate whether fusion has occurred. The fusion indicia can be routed to the antenna 30. The antenna 30 can transmit the fusion indicia to the receiver 50. The receiver 50 can receive the fusion indicia from the antenna 30. Based on the load experienced by the spine, the clinician can determine whether fusion has occurred In some embodiments, the sensor 20, the implant 200, and/or the bone graft material 300 can be a strain gauge type load sensor. The strain gauge is similar to a resistor element, wherein the resistance varies according to the load experienced by the surface to which the sensor 20, the implant 200, and/or the bone graft material 300 is attached. For example, when the surface is tensilely deformed, the resistance of the sensor 20, the implant 200, and/or the bone graft material 300 will increase, and when the surface is compressively deformed, the resistance of the sensor 20, the implant 200, and/or the bone graft material 300 will decrease. During fusion, the load experienced by the intervertebral implant 200, if present, or the bone graft material, if present, is expected to decrease. The fusion between vertebrae will support the load instead of the intervertebral implant 200 or the bone graft material 300. The antenna 30 can transmit the fusion indicia to the receiver 50. The receiver 50 can receive the fusion indicia from the antenna 30. Based on the load experienced by the implant 200, the clinician can determine whether fusion has occurred.

The strain may be directly related to forces applied to and experienced by the sensor 20, the intervertebral implant 200 and/or the bone graft material 300. Monitoring the force applied to the sensor 20, the intervertebral implant 200 and/or the bone graft material 300 over time may allow the doctor to determine whether the spine is healing or whether fusion has occurred. As the spine heals, the amount of load carried by the vertebrae will increase, and the amount of load carried the intervertebral implant 200, if present, or the bone graft material, if present, will decrease. The sensor 20, the implant 200, and/or the bone graft material 300 will measure a lower load as the spine heals. Remedial action, such as subsequent surgery, may be performed if the load does not decrease at the expected rate.

After the diagnostic system 100 is implanted in the disc space, the sensor 20, the implant 200, and/or the bone graft material 300 can sense load when activated. In some embodiments, the sensor 20, the implant 200, and/or the bone graft material 300 can be activated by the power source 40. In other embodiments, the sensor 20, the implant 200, and/or the bone graft material 300 can be self-activated. The sensor 20, the implant 200, and/or the bone graft material 300 can be deactivated for a period of time. The sensor 20, the implant 200, and/or the bone graft material 300 can be reactivated to determine the fusion indicia. In some methods, the diagnostic system 100 can periodically monitor the fusion indicia.

The diagnostic system 100 can include any orthopedic implant, such as bone plates. The implant can be used in repairing fractured bones. The implant can be used in any manner for treating other orthopedic conditions where fusion is desired. Non-spinal applications are contemplated. In non-spinal application, the implant can be shaped and sized for the application. In similar methods to those described above, bones or other joints are connected or fused, such as finger, knee or elbow joints.

What is claimed is:

1. A diagnostic system comprising:
   a spinal implant or graft material configured to be inserted within a disc space between two vertebrae;
   an antenna located in, on or adjacent to the spinal implant, located in, on or adjacent to the graft material, or within the disc space, the antenna configured to send signals to a remote location;
   at least one sensor located in, on or adjacent to the spinal implant, located in, on or adjacent to the graft material, or within the disc space, the at least one sensor configured to measure at least one fusion indicia, wherein the at least one sensor comprises at least one of an oxygen saturation sensor that measures a percentage of hemoglobin binding sites occupied by oxygen molecules, and a light sensor that determine whether a light path has become obstructed by fusion; and
   a receiver configured to receive signals at the remote location, and based on the received signals, determine an extent to which fusion of the two vertebrae has occurred,
   wherein the intervertebral implant is configured to emit electrical current to stimulate bone growth.

2. The diagnostic system of claim 1, further comprising a network that electrically connects the antenna, the at least one sensor, and the receiver.

3. The diagnostic system of claim 1, further comprising a power source located in, on or adjacent to the spinal implant.

4. The diagnostic system of claim 1, further comprising a power source located at the remote location.

5. The diagnostic system of claim 1, wherein the antenna is located on the spinal implant.

6. The diagnostic system of claim 1, wherein the antenna is located on the sensor.

7. The diagnostic system of claim 1, wherein the fusion indicia further comprises at least one of load, strain, and oxygen level.

8. The diagnostic system of claim 1, wherein the at least one fusion indicia is oxygen level.

9. The diagnostic system of claim 1, wherein the at least one fusion indicia is strain.

10. The diagnostic system of claim 1, wherein the at least one fusion indicia is load.

11. The diagnostic system of claim 1, wherein the at least one fusion indicia is light.

12. The diagnostic system of claim 1, wherein the at least one fusion indicia comprises vibration.

13. The diagnostic system of claim 1, wherein the at least one fusion indicia comprises pressure.

14. A method of monitoring fusion of adjacent vertebrae to each other, the method comprising the steps of:
    inserting the intervertebral implant and graft material within a disc space between two vertebrae;
    sensing at least one fusion indicia in, on or adjacent to the implant, in, on or adjacent to the graft material, or within the disc space, wherein the fusion indicia comprises at least one of oxygen saturation to measure a percentage of hemoglobin binding sites occupied by oxygen molecules, and light to determine whether a light path has become obstructed by fusion;

sending signals of the fusion indicia to a remote location with an antenna located in, on or adjacent to the spinal implant, located in, on or adjacent to the graft material, or within the disc space;

receiving the signals with a receiver at the remote location; and based on the received signals, determining an extent to which fusion of adjacent vertebrae has occurred.

15. The method of claim 14, wherein the at least one fusion indicia is strain.

16. The method of claim 14, wherein the at least one fusion indicia is load.

17. The method of claim 14, wherein the at least one fusion indicia is vibration.

18. The method of claim 14, wherein the at least one fusion indicia is pressure.

19. The method of claim 14, wherein the at least one fusion indicia is measured by the implant.

20. The method of claim 14, wherein the at least one fusion indicia is measured by a sensor.

21. The method of claim 14, further comprising expanding the spinal implant within the disc space.

22. The method of claim 14, further comprising emitting electrical current to stimulate bone growth.

23. The method of claim 14, wherein measuring at least one fusion indicia occurs after the surgery.

24. The method of claim 14, wherein measuring at least one fusion indicia occurs one month after surgery.

25. The method of claim 14, wherein measuring at least one fusion indicia occurs one year after surgery.

26. The method of claim 14, wherein the fusion indicia further comprises an oxygen level.

* * * * *